United States Patent [19]

Bernardini

[11] Patent Number: 4,632,115
[45] Date of Patent: Dec. 30, 1986

[54] PORTABLE HEAT TREATMENT SYSTEM AND REFILL UNIT THEREFOR

[75] Inventor: Ronald J. Bernardini, Ambler, Pa.

[73] Assignee: Michael Litman, Philadelphia, Pa.

[21] Appl. No.: 560,345

[22] Filed: Dec. 12, 1983

[51] Int. Cl.⁴ .............................................. D61H 33/00
[52] U.S. Cl. ..................................................... 128/370
[58] Field of Search ............... 128/399, 368, 400, 370, 128/402, 403; 220/408, 409, 410, 419; 126/243, 373; 159/32, 34; D7/151, 360, 393, 394, 395; 24/116 R, 116 A; 220/94 R; 294/68, 170, 171, 172; 219/415

[56] References Cited

U.S. PATENT DOCUMENTS

| | | | |
|---|---|---|---|
| 847,324 | 3/1907 | Ely | 128/370 |
| 1,443,995 | 2/1923 | Lennox | 220/94 R |
| 1,567,618 | 12/1925 | Robinson | 220/94 R |
| 1,863,533 | 6/1932 | Odell | 128/370 |
| 1,957,379 | 5/1934 | App | 220/94 R |
| 2,892,561 | 6/1959 | Frank | 220/94 R |
| 2,904,037 | 9/1959 | Cassidy | 128/370 |
| 3,157,774 | 11/1964 | Moore et al. | 128/370 |
| 3,946,893 | 5/1976 | Bowersmith | 220/94 R |
| 4,284,880 | 9/1981 | Keiser | 219/415 |

FOREIGN PATENT DOCUMENTS 605828  9/1960  Canada ............................... 24/116.1

Primary Examiner—William E. Kamm
Attorney, Agent, or Firm—Caesar, Rivise, Bernstein, Cohen & Pokotilow

[57] ABSTRACT

A refill unit usable in conjunction with a heating shoe of a portable heat treatment system to provide heat therapy to a part of the human body. The unit includes a heat conductive container having a base and peripheral walls extending upwardly from the base to define an internal compartment. A solid body treating material only partially fills the compartment and is adapted to be melted by use of the heating shoe to provide heat therapy to a part of the body. Opposed peripheral walls of the container include upper bent edges to provide opposed handle-retaining channels in which handles are received and retained.

7 Claims, 4 Drawing Figures

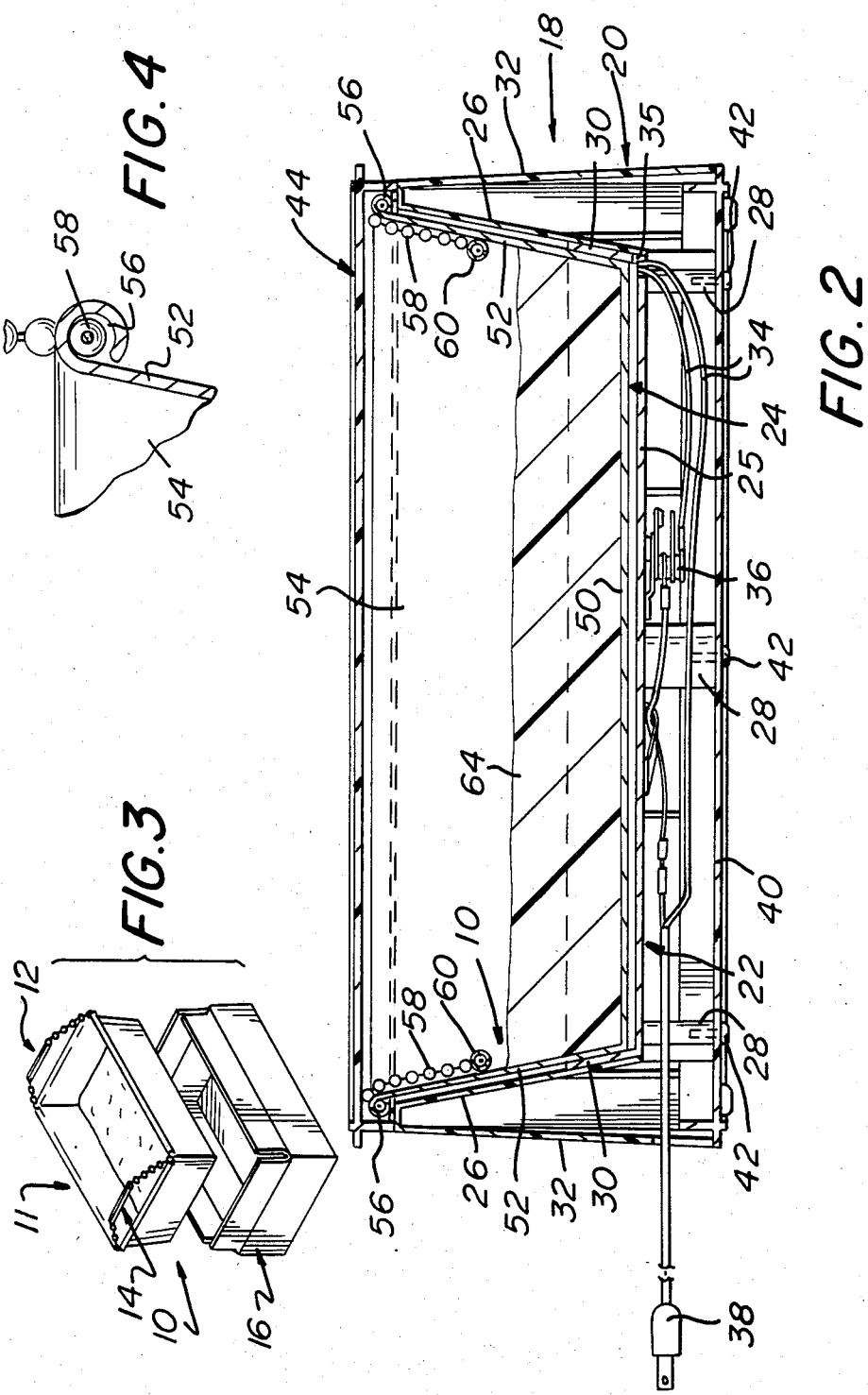

PORTABLE HEAT TREATMENT SYSTEM AND REFILL UNIT THEREFOR

FIELD OF INVENTION

This invention relates generally to the field of providing heat treatment to parts of the human body, and more specifically, to a refill unit employed in a portable heat treatment system utilized for this purpose.

BACKGROUND OF THE INVENTION

A unique portable heat treatment system for providing heat therapy to parts of the human body has been invented by Ronald J. Bernardini, and is described and claimed in U.S. patent application Ser. No. 376,000 filed on May 7, 1982. One of the unique aspects of that system is its use of a throw-away refill unit in which the body treating material is contained. In the preferred form of the invention the body treating material includes paraffin wax, and the system is utilized to provide relief for a multitude of ailments, as is well known.

Although the portable heat treatment system disclosed in the above-mentioned Bernardini patent application does employ a refill unit, a need exists to improve the handleability of the unit for both insertion and removable from its supporting heating shoe. Moreover, it is extremely important that any modifications provided to make the unit easier to handle be accomplished without excessively increasing the fabrication and/or the material costs of the system. It is to such an improved refill unit that the present invention is directed.

OBJECTS OF THE INVENTION

It is a general object of this invention to provide an improved refill unit for portable heat treatment systems utilized to provide heat therapy to parts of the human body.

It is a more specific object of this invention to provide a refill unit and a portable heat treatment system which is easy to handle and economical to fabricate.

SUMMARY OF THE INVENTION

The above and other objects of this invention are achieved with a refill unit intended to be used in conjunction with a heating shoe of a portable heat treatment system to provide heat therapy to a part of the human body, wherein the unit includes a heat conductive container having a base and peripheral walls extending upwardly from the base to define an internal compartment. A solid body treating material only partially fills the the compartment of the container, and this material is adapted to be melted by the heating shoe for use in providing heat therapy to the desired parts of the human body. Opposed peripheral walls each include an upper bent edge providing a handle-receiving channel as part of the container. A continuous flexible member is retained within the opposed handle-receiving channels to provide oppositly disposed handles for enhancing the handleability of the refill unit.

Other objects and many of the attendant advantages of this invention will be readily appreciated as the same becomes better understood by reference to the following detailed description when considered in connection with the accompanying drawings.

DESCRIPTION OF THE DRAWINGS

FIG. 2 is a sectional view taken along line 2—2 of FIG. 1 with the elements in assembled position;

FIG. 3 is an exploded isometric view showing the refill unit of this invention relative to its retaining package; and FIG. 4 is an enlarged sectional view taken along line 4—4 of FIG. 1.

DESCRIPTION OF THE BEST MODE OF THE INVENTION

Figure 1:
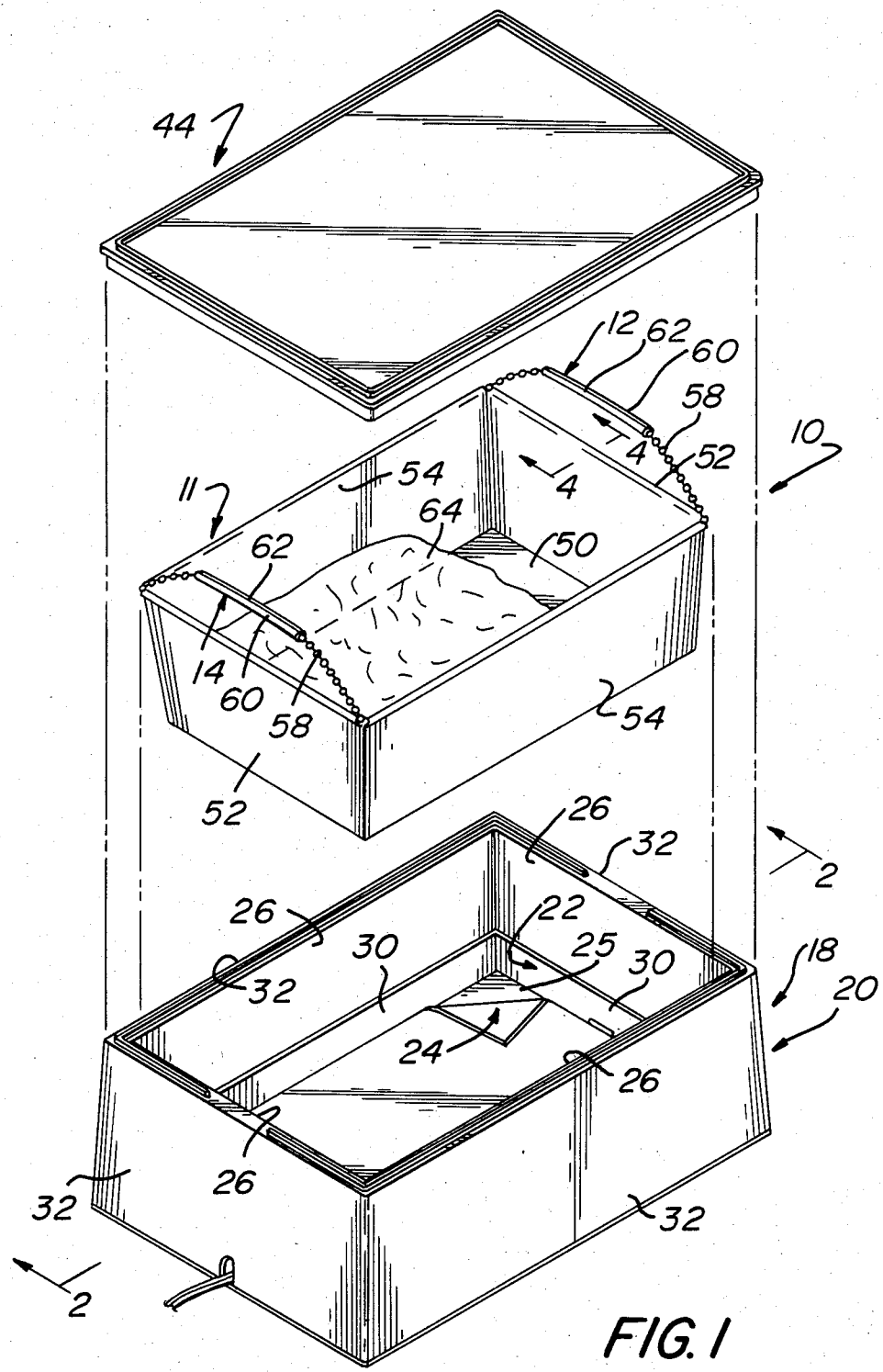
FIG. 1 is an exploded isometric view of a refill unit of this invention shown relative to a supporting heating shoe and topcover plate of the portable heat treatment system in which the refill unit is intended to be employed.

Referring now in greater detail to the various figures of the drawings wherein like characters refer to like parts, a refill unit embodying the present invention is generally shown at 10 in FIG. 3. The refill unit 10 basically is in the form of a container 11 including handles 12 and 14 disposed adjacent opposed ends thereof to assist in the manipulation, or handling of the refill unit, as is necessary. The refill unit 10 can be packaged in any suitable manner, and in the illustrated embodiment is retained within a conventional paperboard carton 16.

The refill unit 10 of this invention is adapted to be utilized in connection with a portable heat treatment system of the type invented by Ronald J. Bernardini, and disclosed and claimed in U.S. Pat. No. 376,000. This latter patent application is herein incorporated by reference.

For ease of reference the general arrangement of the portable heat treatment system adapted for use with the refill unit 10 of this invention will be described herein. However, for further details reference should be had to the above-referenced Bernardini patent application.

Referring specifically to FIGS. 1 and 2 the refill unit 10 of this invention is intended to be supported in a heating shoe 18. The heating shoe includes a plastic housing 20 which preferably is injection molded as a single unit. In addition the shoe includes a heat conductive base member 22 retained within the plastic housing 20, and a flexible heater 24 adhered to the bottom wall 25 of the base member.

The plastic housing 20 includes inner peripheral walls 26 which extend upwardly and diverge outwardly from lower spaced support members 28 that are adapted to support the bottom wall 25 of the base member 22. The inclination of the inner peripheral walls 26 is intended to match the outward inclination of peripheral walls 30 of the conductive base member 22, as can be seen best in FIG. 2. The plastic housing 20 further includes outer peripheral walls 32 forming a continuous injection molded extension of the inner peripheral walls.

Referring specifically to FIG. 2 conductive leads 34 from the flexible heater 24 extend through an opening 35 in the base member 22 located at a junction of the bottom wall 25 of said base member with an adjacent peripheral wall 30. These conductive leads 34 are electrically connected through a thermostat 36 to a conventional plug 38 adapted to be connected to a conventional electrical receptacle. The conductive leads 34 are enclosed by a bottom plate 40 which is secured to the plastic housing 20 of the eating shoe by conventional screws 42 received within threaded passages located in the spaced support members 28. A top cover plate 44 is provided for closing the portable heat treatment system to thereby prevent contamination of the body treating material 64 located in the refill unit 10.

Referring specifically to FIGS. 1 and 2 the refill unit 10 of this invention is adapted to be supported within the heating shoe 18 solely by gravity, with a base, or bottom wall 50 of the container 11 being supported on the flexible heater 24. The container 11 further includes peripheral end walls 52 and peripheral side walls 54 which extend upwardly and diverge outwardly from the bottom wall 50. The angle of divergence of the container end and side walls is substantially the same as the angle of divergence of the inner peripheral walls 26 of the plastic housing 20 so that the container will be supported in a stable manner within the housing.

As can be seen best in FIGS. 2 and 4 the upper edges of the peripheral walls 52 and 54 of the heat conductive container 11 are bent, such as by rolling, to form hollow elongate channels, or chambers 56 circumscribing the upper periphery of the container. The container 11 can be in the form of a conventional meat pan having a rolled upper end to provide a smooth, exposed periphery. However, in accordance with this invention it is only necessary to provide bent upper ends adjacent either the opposed peripheral end walls 52 or adjacent the opposed peripheral side walls 54 for the purpose of receiving a pair of opposed handles 12 and 14.

Referring specifically to FIGS. 1 and 2 each of the handles 12 and 14 of this invention is provided by a flexible member 58, preferably in the form of a ball chain having a conventional clasp (not shown). In the most preferred embodiment of this invention a No. 1 metal ball chain has been employed with success. It is very desirable that the flexible members 58 be sized to be retained within their respective channels 56 without falling out of any gap or space that may exist between the marginal edge of the rolled lip and the adjacent peripheral wall of the container (See FIG. 4).

The structure of each handle is completed by a sleeve 60, preferably made of plastic, which is split at 62 to permit it to be snapped about its respective ball chain and thereby provide a comfortable heat insulating gripping member. These split plastic sleeves 60 can be of the snap-lock type sold by Allen Fields Company located in New York City, N.Y.

Referring to FIG. 2 the refill unit includes a solid body treating material 64 only partially filling the interior compartment of the container 11 and adapted to be melted by the heating shoe for use in heat therapy applications. It should be noted that the length of the flexible members 58 employed to form the handles 12 and 14 are chosen so that they can be disposed within the interior of the container 11 above the upper level of the solid body treating material 64. This permits the handles to be conveniently stored when they are not in use without unduly contaminating them with the body treating material. In the most preferred embodiment of this invention the body treating material 64 can be a paraffin wax which also can include other substances such as lanolin to assist in protecting or treating the skin of the user.

Without further elaboration the foregoing will so fully illustrate my invention that others may, by applying current or future knowledge, adopt the same for use under various conditions of services.

I claim:

1. A refill unit usable in conjunction with a heating shoe of a portable heat treatment system to provide heat therapy to a part of the human body; characterized in that said unit includes a heat conductive container having a base and peripheral walls extending upwardly from said base to define an interior compartment, a material for treating parts of the human body only partially filling the compartment, said material being in a solid state at room temperature and being adapted to be melted within the heating shoe for use in providing heat treatment therapy to a part of the human body, opposed peripheral walls of said container each including an upper bent edge defining a handle-retaining channel, and a pair of handle members, each of said members extending through opposed ends of a respective channel and having a section between the opposed ends adapted to be engaged for the purpose of transporting said refill unit, said section of each handle member being positionable within the interior compartment of the container and being dimensioned to be above the level of the body treating material when positioned within said interior compartment.

2. The refill unit of claim 1 characterized in that each handle includes a flexible chain and a plastic gripping member encircling said chain.

3. The refill unit of claim 2 characterized in that the chain is a metal ball chain and the plastic gripping member is a split plastic sleeve encircling the chain.

4. A refill unit usable in conjunction with a heating shoe of a portable heat treatment system to provide heat therapy to a part of the human body; characterized in that said unit includes a heat conductive container having a base and peripheral walls extending upwardly from said base to define an interior compartment, a material for treating parts of the human body only partially filling the compartment, said material being in a solid state at room temperature and being adapted to be melted within the heating shoe for use in providing heat therapy to a part of the human body, said peripheral walls including opposed side walls and opposed end walls, said opposed end walls being shorter than said opposed side walls for defining a substantially rectangular interior compartment, and upper edges of said opposed end walls each being rolled to provide a substantially cylindrical handle-retaining channel therein, a handle disposed adjacent each of the end walls of the container, each handle including a member extending through opposed ends of a respective cylindrical handle-retaining channel and being confined within said channel for preventing it from inadvertently separating from the container each member including a section between the opposed ends adapted to be engaged for the purpose of transporting said refill unit, said section of each member being positionable within the interior compartment of the container and being dimensioned to be above the level of the body treating material when positioned within said interior compartment.

5. The refill unit of claim 4 characterized in that each handle includes a flexible chain and a plastic gripping member encircling said chain.

6. The refill unit of claim 5 characterized in that the chain is a metal ball chain and the plastic gripping member is a split plastic sleeve encircling the chain.

7. A portable heat treatment system including a portable heating shoe, a cover for said heating shoe, and a refill unit removable retained within said heating shoe, said refill unit including a heat conductive container having a base and peripheral walls extending upwardly from said base to define an interior compartment, a material for treating parts of the human body only partially filling the compartment, said material being in a solid state at room temperature and being adapted to be melted within the heating shoe for use in providing heat treatment therapy to a part of the human body, opposed peripheral walls of said container each including an upper bent edge defining a handle-retaining channel, and a handle member extending through opposed ends of each of said channels and having a section between the opposed ends adapted to be engaged for the purpose of transporting said refill unit, said section of each handle member being dimensioned to be above the level of the body treating material when disposed within the interior compartment of the container, each of said sections being disposed within the interior compartment of the container when said refill unit is within the heating shoe and the cover closes said shoe.

* * * * *